ively, although monobromodifluoromethyl, monochlorodifluoromethyl, trifluoromethyl and perfluoroethyl are preferred. The trifluoroalkene reactant is suitably obtained by fluorination of a tetrahalomethane with a metal monofluoride such as mercuric monofluoride. The trifluoroalkene reactant is employed in admixture with the olefin reactant which comprises an alkene of from 2 to 4 carbon atoms inclusive, preferably of 2 or 3 carbon atoms. Illustrative of such olefin reactants are ethylene, propylene, 1-butene and 2-butene. Of the olefin reactants, ethylene and propylene are preferred and ethylene is particularly preferred. The molar ratio of olefin reactant to trifluoroalkene reactant is not critical. Molar ratios of olefin to trifluoroalkene from about 0.1:1 to about 10:1 are satisfactory with molar ratios from about 0.5:1 to about 5:1 being preferred.

The catalyst is a homogeneous palladium (II) catalyst, i.e., a compound of divalent palladium soluble in the reaction mixture. Illustrative of such palladium (II) compounds are the palladium (II) halides such as palladium (II) chloride, palladium (II) bromide and palladium (II) iodide, as well as palladium (II) acetate, palladium (II) sulfate, palladium (II) nitrate, palladium (II) acetylacetonate and bis(benzonitrile)palladium (II) chloride. Preferred palladium (II) catalysts include palladium (II) chloride and palladium (II) acetate.

The catalyst is employed in catalytic quantities. Typical amounts of catalyst include from about 0.001 mole to about 0.1 mole of palladium (II) catalyst per mole of trifluoroalkene reactant, with amounts from about 0.01 mole to about 0.05 mole of catalyst per mole of trifluoroalkene being preferred.

TRIFLUOROALKENES AND A METHOD FOR THEIR PREPARATION

This is a continuation of application Ser. No. 887,454, filed July 21, 1986, now abandoned, which is a division of application Ser. No. 780,522, filed Sept. 25, 1985, now abandoned.

BACKGROUND OF THE INVENTION

The present invention is directed to certain trifluoroalkene compounds. Of particular interest are compounds of the formula $RCF_3$ where R is a $C_4$ to $C_7$ unsaturated alkyl radical. The invention is also particularly directed to the preparation of such compounds in high selectivity by an addition reaction of lower ($C_3$ or $C_4$) trifluoroalkenes with lower olefins.

Fluorinated hydrocarbons such as those of this invention are known to have utility as refrigerants, pesticides, dielectric fluids, heat transfer fluids, solvents, and intermediates in various chemical reactions, including polymerization.

Methods are known in the art for the preparation of a variety of fluorocarbons (compounds containing only carbon and fluorine atoms) and partially-fluorinated hydrocarbons (compounds containing carbon, hydrogen and fluorine atoms), the latter group specifically including the one trifluoroalkene compound 3,3,3-trifluoropropene.

According to U.S. Pat. Nos. 3,062,901 and 3,067,263 and prior art cited therein, at least five different approaches have been proposed for the preparation of 3,3,3-trifluoropropene. U.S. Pat. No. 3,062,901 discloses and claims a process in which ethane is contacted at a temperature from about 250° to 700° C. with a compound of the formula $CF_3X$ wherein X is chlorine or bromine. U.S. Pat. No. 3,067,263 describes and claims a similar process for the contact of ethylene with $CF_3X$ at a temperature from about 600° to 1000° C. This process is shown to have a low yield of the desired trifluoropropylene, with the principal product of the reaction being the side product $CF_3H$. These two patents also teach that 3,3,3-trifluoropropene can be prepared in a multi-step process including steps for converting ethyl trifluoroacetate to trifluoroacetone, reducing the trifluoroacetone to the alcohol, and dehydrating the alcohol to 3,3,3-trifluoropropene. Another method disclosed in these patents involves the free radical addition of $CF_3I$ to ethylene in the presence of a catalyst followed by dehydroiodination. Still another method described involves reacting $CCl_4$ with HBr in the presence of a catalyst to product $CCl_3$—$CH_2$—$CH_2Br$ and reacting this intermediate with hydrogen fluoride.

Insofar as is known, it has not been suggested that either such methods can be extended to the preparation of the higher trifluoroalkene compounds as are of interest in the present invention.

Other prior art generally relevant to aspects of this invention pertaining to fluorinated hydrocarbons and their preparation, includes the disclosure in U.S. Pat. No. 3,456,025 of the preparation of gem-difluoroalkenes (1,1-difluoroalkenes) by dehydrofluorination of trifluoroalkanes in the presence of a fluorided alumina catalyst at a temperature in the range from 500° to 1200° C. U.S. Pat. No. 2,551,639 teaches methods for the condensation of 2-olefins with polyhalogenated alkanes to produce mixtures of different unsaturated halogenated compounds. U.S. Pat. No. 2,709,183 describes the direct reaction of hydrogen fluoride with carbon compounds at high temperature (i.e., at least 2500° C.). U.S. Pat. Nos. 2,637,747, 2,767,227, and 3,904,701 teach different methods for the preparation of trifluoroethane and related compounds. U.S. Pat. No. 3,755,477 is directed to a gas-phase reaction of hydrogen fluoride with halogenated alkanes or halogenated alkenes in the presence of a chromium oxide catalyst.

In one important aspect, the invention centers upon the use of certain palladium catalysts to promote the reaction between an olefin reactant and a trifluoroalkene reactant. As described in U.S. Pat. No. 4,436,946 and other prior art cited therein, palladium compounds are known in the art to catalyze the conversion of lower olefins to their dimers and other oligomerizers.

SUMMARY OF THE INVENTION

It has now been found that trifluoroalkenes of the formula $RCF_3$, where R is an unsaturated alkyl radical of 4 of more carbon atoms can be prepared by the reaction of one or more $C_3$ or $C_4$ trifluoroalkenes with one or more $C_2$ to $C_4$ olefins. For purposes of the invention, this reaction is necessarily carried out in the liquid phase and in the presence of a cationic palladium catalyst.

Accordingly, the present invention can, in part, be briefly described as a process for the preparation of $C_5$ and higher trifluoroalkenes which comprises a step for contacting one or more $C_2$ to $C_4$ monoolefins with one or more $C_3$ or $C_4$ trifluoroalkenes in the liquid phase and in the presence of a soluble palladium (II) catalyst.

Under preferred conditions, this process has a high selectivity for production of the higher trifluoroalkene cross dimers of the olefin and lower trifluoroalkene reactants. This selectivity is considered surprising, in light of the high degree of activity which palladium (II) compounds have catalyzing the conversion of propylene alone (i.e., in the absence of the trifluoroalkene reactant) to propylene dimers, and further in light of the finding that trifluoroalkenes alone (i.e., in the absence of the olefin reactant) are unreactive over such palladium catalysts.

The invention also encompasses novel higher trifluoroalkene products of this process. Of particular interest are the compounds of the formula $RCF_3$, where is an unsaturated alkyl radical of 4 to 7 carbon atoms, more particularly compounds of the formula $C_6H_9F_3$ and the formula $C_7H_{11}F_3$, which result, for instance, from the cross dimerization reactions of propylene and butylenes, respectively, with 3,3,3-trifluoropropene, and most particularly the trifluorohexenes and trifluoroheptenes having linear carbon structure.

DESCRIPTION OF THE PREFERRED EMBODIMENTS

The process of this invention necessarily utilizes both a lower aliphatic mono-olefin reactant and a lower trifluoroalkene reactant. The class of suitable olefin reactants comprises one or more elefins of 2 to 4 carbon atoms and specifically includes ethylene, propylene, 1-butylene, 2-butylene and isobutylene. Ethylene, propylene, and 1-butylene form a preferred class of olefin reactants. Particularly good results have been obtained using propylene and 1-butylene as reactants, while propylene is particularly preferred for purposes of the invention. Mixtures of these compounds are also suitable for use as the olefin reactant.

In order to prepare the (higher) trifluoroalkene compounds of the invention, the (lower) trifluoroalkene reactant suitably comprises one or more trifluoroalkene compounds of the formula R—CF$_3$, where R is an alkenyl radical of either 2 or 3 carbon atoms. This class of suitable reactants specifically includes 3,3,3-trifluoropropene, 3,3,3-trifluoro-1-methylpropene, 4,4,4-trifluorobutene, and 4,4,4-trifluoro-2-butene, as well as mixtures of these compounds. A reactant having the trifluoromethyl group is considered a critical element of the process of the invention; corresponding compounds in which any one or more of the fluorine atoms is replaced by another halogen atom, for instance, by chlorine or bromine are not considered suitable reactants. Most preferably, the reactant consists essentially of 3,3,3-trifluoropropene. (As the term trifluoroalkene is used herein, it is intended to represent either a lower carbon number reactant or a higher carbon number product having a single trifluoromethyl substituent.)

The process of the invention for preparation of the higher trifluoroalkene compounds of interest necessarily involves contact between the olefin and trifluoroalkene reactants in the presence of a catalytically effective amount of a palladium (II) catalyst, particularly a soluble palladium (II) compound. Examples of suitable palladium catalysts include palladium nitrate, palladium sulfate, palladium halides, palladium carboxylates. Also suitable as catalyst in the invention are palladium salts of acids characterized by a pKa of less than 2. Preference can be expressed for palladium carboxylates of carboxylic acids having no more than about 12 carbon atoms, while palladium acetate is particularly preferred.

Complexes of palladium compounds with chelating ligands are in many cases preferred to enhance catalyst solubility. Specific examples of such complexes include tetrakisacetonitrile palladium fluoroborate, tetrakis(triphenylphosphine)palladium, bis(tri-o-tolylphosphine) palladium acetate, and bis(tri-phenylphosphine)palladium sulfate. As a general rule, useful chelating ligands are organic compounds containing as coordinating atoms at least two atoms of elements of Group Va of the Periodic Table, particularly the elements nitrogen, phosphorus and arsenic of this group, which are connected through a chain comprising 2 to 6 carbon atoms.

Likewise, other soluble palladium complexes are also suitable, including, for example, bis(2,4-pentanedionato)palladium, bis(picolinato)palladium, palladium hydride complexes, and palladium olefin complexes such as di-μ-chlorodichlorobis(ethlyene)dipalladium ([Pd.C$_2$H$_4$.Cl$_2$]$_2$), and di-μ-chlorodichlorobis(propylene)-dipalladium ([Pd.C$_3$H$_6$.Cl$_2$]$_2$).

Further examples of suitable palladium compounds and complexes are provided in the commonly-assigned co-pending application of E. Drent, Ser. No. 754,882 filed July 15, 1985, the disclosure of which on this subject is incorporated herein by this reference thereto. The Ser. No. 754,882 application describes and claims a process for the dimerization of olefins such as propylene in the presence of palladium chelate complex catalysts.

In the preparation process of the invention, the catalyst is necessarily applied in liquid solution, preferably in a liquid medium comprising an added solvent (i.e., a solvent other than the olefin and trifluoroalkene reactants). Aprotic organic solvents are particularly preferred for this service. Examples of suitable added solvents include hydrocarbons such as hexane, cyclohexane, octane, cyclo-octane, benzene, toluene, the xylenes, ethylbenzene, cyanogen, chlorinated hydrocarbons such as chlorobenzene and dichlorobenzene, perfluoroalkanes, ethers such as tetrahydrofuran, dimethylether or diethylene glycol (diglyme), methyl-t-butylether and dioxane, nitro compounds such as dimethylformamide, nitromethane and nitrobenzene, and sulfones such as sulfolane. The use of acetonitrile, nitromethane, and sulfolane solvents is considered most preferred. Preference may also be expressed for solvents which aid in the separation of trifluoroalkene products from the product mixture of the process. When the process is conducted using a sulfolane solvent, for instance, the product trifluoroalkenes form a separate liquid phase.

In one preferred mode of operation of the process of the invention, the catalyst and solvent solution is introduced into a reactor and contacted with a gaseous mixture of the olefin and trifluoroalkene reactants. In such a case, the process is suitably carried out at a pressure in the range from about 20 to 2000 psig, with pressures in the range from about 300 to 1500 psig being considered preferred. Higher pressures may be applied, if desired, to increase the concentration of the reactants in the liquid reaction mixture and also the rate of the cross dimerization reaction. The process is very suitably practiced at a temperature up to about 200° C., and preferably a temperature in the range from about 0° to 200° C., while a temperature between about 20° and 130° C. is more preferred, and a temperature between about 30° and 120° C. is considered most preferred.

Relative proportions of reactants and catalyst are not a critical aspect of the preparation of the cross dimers. As a general rule, preference can be expressed for a contact in which the molar ratio of olefin reactant to trifluoroalkene reactant is at least about 0.5 to 1. In order to enhance the selectivity of the cross dimerization reaction relative to the production of byproducts such as olefin dimers and the cross dimers formed by a reaction of olefin with product trifluoroalkenes, it is also preferred to operate the process with a mixture which comprises the reactants in a molar ratio of olefin to trifluoroalkene reactants which is between about 0.5 to 1 and 10 to 1. A reactant molar ratio of about 0.8 to 1 to about 2 to 1 is considered still more preferred, while a molar ratio of about 1 to 1 is considered most preferred.

The palladium catalyst is typically effective for purposes of the invention in solution in the liquid solvent medium in a concentration generally in the range from about $10^{-6}$ to about $10^{-1}$ mole of palladium compound per mole of reactants. Palladium catalyst concentrations in the liquid medium between about $10^{-5}$ and $10^{-2}$ mole per mole of reactants are considered preferred.

It is considered particularly surprising that the process of the invention yields the cross dimerization product of the olefin reactant and the trifluoroalkene reactant in high selectivity. In the absence of trifluoroalkene reactant, palladium compounds and complexes are very active catalyst for the conversion of lower olefins to their dimers and higher oliogomers and polymers. However, olefin dimers and oligomers account for only a small fraction of the product obtained by preferred practices in accordance with the process of the invention. Moreover, in the absence of olefin reactant, the trifluoroalkene reactant is essentially unreactive in the presence of palladium catalysts and under conditions suitable for the invention.

In certain preferred embodiments, the invention is particularly directed to higher trifluoroalkene products having a linear (i.e., straight chain rather than branched chain) carbon structure. Most preferably, the invention is directed to the processing of propylene and trifluoropropylene reactants to yield trifluorohexene having substantially linear carbon structure, or to the processing of 1-butylene and trifluoropropylene to yield linear trifluoroheptene.

The invention is now further illustrated by the following examples of specific higher trifluroalkenes and methods for their preparation. These examples represent particular preferred embodiments of the invention and are not intended to limit its broader scope.

EXAMPLES 1–8

A series of preparations were made of higher trifluorohexenes according to the invention.

For Example 1, a gaseous mixture of propylene (14.0 g, 0.33 mole) and 3,3,3-trifluoropropylene (30.7 g, 0.32 mole) was introduced into a stainless steel autoclave reactor containing a liquid solution of tetrakisacetonitrile palladium (II) fluoroborate in 9 ml of sulfolane solvent. The tetrakisacetonitrile palladium (II) fluoroborate solution had been prepared according to the precedures of R. F. Schramm and B. F. Wayland, Chemical Communications, 1968, p. 898. The gas phase of the reactor was stirred while reactor contents were maintained at ambient temperature (about 21° C.) and at a pressure which varied from about 80 psig to 100 psig. After 115 hours in the autoclave, 13.7 g of the reactants had been converted to form a separate liquid product phase. Overall selectivity to $C_6$ products was about 99%. Of the $C_6$ products, about 94% were trifluorohexene cross dimers of the propylene and trifluoropropylene reactants. The major fraction of the cross dimer was characterized by a linear carbon structure. The principal byproducts were hexenes, in a selectivity of only about 3%.

Examples 2–8 were caired out in a similar manner, with variations in reaction temperature, pressure, solvent and reactant quantities, and reaction times. In each example, the catalyst was tetrakisacetonitrile palladium II fluoroborate, in a quantity of 0.5 grams. The process conditions and results for Examples 1–8 are summarized in the following Table.

A second comparative experiment was carried out in which the reactor was charged with 9 ml of solvent, 26 g of propylene, and 0.5 g of catalyst. No 3,3,3-trifluoropropylene reactant was introduced. After 4 hours reaction at 70° C., 76% of the propylene had been converted to olefin dimers and oligomers. The product contained about 81% hexenes, about 14% nonenes and about 4% dodecenes.

EXAMPLE 7

A higher trifluoroalkene product was prepared according to the invention by a cross dimerization reaction between a 3,3,3-trifluoropropylene reactant and an ethylene reactant. An equimolar mixture of the trifluoropropylene (21.5 g) and the ethylene (8.9 g) was introduced into an autoclave reactor containing 9 ml of sulfolane solvent and 0.5 g of tetrakisacetonitrile palladium II fluoroborate catalyst. After stirring of the gaseous reactants phase over the catalyst solution for 4 hours at a temperature of 50° C. and a pressure of 120–540 psig, 40% of the reactants had been converted to a mixture of 23% hydrocarbons, which were dimers and oligomers of ethylene, and 76% of higher trifluoroalkenes. The trifluoroalkenes fraction contained about 38% trifluoropentenes, about 9% trifluorohexenes, and about 34% trifluoroheptenes.

EXAMPLE 8

In a further example of the invention, an equimolar mixture of butene (13.7 g) and 3,3,3-trifluoropropylene (19.5 g) was contacted in the autoclave with a solution of 0.5 g of the tetrakisacetonitrile palladium II fluoroborate in 9 ml of sulfolane. After 4 hours at 50° C., 16.6% of the reactants were converted to a mixture of 19% octenes and 81% higher trifluoroalkenes (6% trifluorohexenes and 75% trifluoroheptenes).

I claim as my invention:

1. A selective process for the preparation of trifluoroalkenes of the formula $RCF_3$, wherein R is $C_5$ to $C_6$ unsaturated alkyl, which comprises contacting and reacting 3,3,3-trifluoropropylene with one or more $C_3$ to $C_4$ olefins in the presence of a liquid solution of one or more palladium (II) compounds.

|  | Example | | | | | |
|---|---|---|---|---|---|---|
|  | 1 | 2 | 3 | 4 | 5 | 6 |
| Temperature (°C.) | 21 | 50 | 50 | 50 | 50 | 70 |
| Pressure (psig) | 80–100 | 150–200 | 125–225 | 100–300 | 120–270 | 75–325 |
| Reaction time (hr.) | 115 | 4 | 17 | 21 | 4 | 4 |
| Volume of solvent (ml) | 9 | 9 | 20 | 20 | 20 | 9 |
| Propylene (g) | 14 | 28 | 46 | 22 | 12 | 6 |
| 3,3,3-trifluoropropylene (g) | 31 | 5 | 92 | 27 | 25 | 16 |
| Conversion (%) | 30 | 43 | 18 | 94 | 32 | 97 |
| Selectivity to $C_6$ products | 99 | 93 | 98 | 94 | 93 | 69 |
| Selectivity to cross dimer (%) | 94 | 32 | 93 | 98 | 97 | 92 |

COMPARATIVE EXPERIMENTS A AND B

A comparative experiment (not in accordance with the invention) was carried out under the same general procedures as those of Examples 1–6, although without the introduction of propylene reactant into the reactor. The reactor was charged with 9 ml of solvent, 29 g of 3,3,3-trifluoropropylene, and 0.5 g of the catalyst. No reaction was observed after 24 hours at 50° C.

2. The process of claim 1, wherein the 3,3,3-trifluoropropylene is contacted with the one or more olefins in the presence of one or more palladium (II) complexes with one or more chelating ligands.

3. The process of claim 1, wherein the contact takes place in an aprotic organic solvent.

4. The process of claim 1, which comprises contacting 3,3,3-trifluoropropylene with propylene in the presence of the one or more palladium (II) compounds.

5. The process of claim 4, wherein the one or more trifluoroalkene compounds are contacted with the propylene in the presence of at least one palladium (II) compound in the form of a complex with a chelating ligand.

6. The process of claim 5, wherein the contact takes place in an aprotic organic solvent.

7. A selective process for the preparation of trifluoroalkenes of the formula $RCF_3$, wherein R is $C_5$ to $C_6$ unsaturated alkyl, which comprises contacting and reacting 3,3,3-trifluoropropylene with one or more $C_3$ to $C_4$ olefins in the presence of a liquid solution of a tetrakisacetonitrile palladium (II) fluoroborate catalyst.

* * * * *